United States Patent
Hu et al.

(10) Patent No.: US 12,277,709 B2
(45) Date of Patent: Apr. 15, 2025

(54) PORTABLE ELECTRONIC DEVICE AND WOUND-SIZE MEASURING METHOD USING THE SAME

(71) Applicant: Wistron Corp., New Taipei (TW)

(72) Inventors: Wen Hsin Hu, New Taipei (TW); Ji-Yi Yang, New Taipei (TW); Zhe-Yu Lin, New Taipei (TW); Hui Chi Hsieh, New Taipei (TW); Yin Chi Lin, New Taipei (TW); Chi Lun Huang, New Taipei (TW)

(73) Assignee: WISTRON CORP., New Taipei (TW)

( * ) Notice: Subject to any disclaimer, the term of this patent is extended or adjusted under 35 U.S.C. 154(b) by 560 days.

(21) Appl. No.: 17/535,622

(22) Filed: Nov. 25, 2021

(65) Prior Publication Data

US 2023/0058754 A1 Feb. 23, 2023

(30) Foreign Application Priority Data

Aug. 18, 2021 (TW) ................. 110130445

(51) Int. Cl.
*G06K 9/00* (2022.01)
*G06F 18/23* (2023.01)
(Continued)

(52) U.S. Cl.
CPC ............ *G06T 7/0016* (2013.01); *G06F 18/23* (2023.01); *G06N 3/08* (2013.01); *G06T 7/11* (2017.01);
(Continued)

(58) Field of Classification Search
None
See application file for complete search history.

(56) References Cited

U.S. PATENT DOCUMENTS 10,605,597 B1   3/2020   Lin
2016/0284084 A1  9/2016   Gurcan et al.
(Continued)

FOREIGN PATENT DOCUMENTS

CN   104161522 A   11/2014
CN   111067531 A   4/2020
(Continued)

OTHER PUBLICATIONS

Extended European Search Report dated Jun. 7, 2022, issued in application No. EP 21216768.8.
(Continued)

*Primary Examiner* — Wei Wen Yang
(74) *Attorney, Agent, or Firm* — McClure, Qualey & Rodack, LLP

(57) ABSTRACT

A wound-size measuring method for use in a portable electronic device is provided. The method includes the following steps: obtaining an input image via a camera device of the portable electronic device; using a CNN (convolutional neural network) model to recognize the input image, and selecting a part of the input image with the highest probability of containing a wound as an output wound image; and calculating an actual height and an actual width of the output wound image according to a lens-focal-length parameter reported by an operating system running on the portable electronic device, a plurality of reference calibration parameters corresponding to a pitch angle of the portable electronic device, and a pixel-height ratio and a pixel-width ratio of the output wound image.

20 Claims, 12 Drawing Sheets

(51) Int. Cl.

| | | |
|---|---|---|
| *G06N 3/08* | (2023.01) | |
| *G06T 7/00* | (2017.01) | |
| *G06T 7/11* | (2017.01) | |
| *G06T 7/62* | (2017.01) | |
| *G06T 7/73* | (2017.01) | |
| *G06T 7/80* | (2017.01) | |
| *G06V 10/22* | (2022.01) | |
| *G06V 10/75* | (2022.01) | |
| *G06V 10/94* | (2022.01) | |
| *G16H 30/40* | (2018.01) | |
| *H04N 17/00* | (2006.01) | |
| *H04N 23/63* | (2023.01) | |
| *H04N 23/80* | (2023.01) | |

(52) U.S. Cl.
CPC .................. *G06T 7/62* (2017.01); *G06T 7/74* (2017.01); *G06T 7/80* (2017.01); *G06V 10/225* (2022.01); *G06V 10/751* (2022.01); *G06V 10/95* (2022.01); *G16H 30/40* (2018.01); *H04N 17/002* (2013.01); *H04N 23/63* (2023.01); *H04N 23/80* (2023.01); *G06T 2207/10024* (2013.01); *G06T 2207/20076* (2013.01); *G06T 2207/20081* (2013.01); *G06T 2207/20084* (2013.01); *G06T 2207/30004* (2013.01); *G06T 2207/30244* (2013.01)

(56) References Cited

U.S. PATENT DOCUMENTS

| | | |
|---|---|---|
| 2018/0132726 A1 | 5/2018 | Dickie et al. |
| 2020/0121245 A1* | 4/2020 | Barclay ................. A61B 5/015 |
| 2021/0277732 A1* | 9/2021 | Parmeshwar ......... E21B 19/165 |

FOREIGN PATENT DOCUMENTS

| | | | |
|---|---|---|---|
| TW | 693829 B | 5/2020 | |
| TW | 1693829 B | 5/2020 | |
| WO | WO-2021076628 A1 * | 4/2021 | ........... A61B 5/0077 |
| WO | WO-2022248964 A1 * | 12/2022 | ........... A61B 5/0077 |

OTHER PUBLICATIONS

Gamage, H.V.L.C., et al.; Instance-Based Segmentation for Boundary Detection of Neuropathic Ulcers Through Mask-RCNN; LNCS 11731; Sep. 2019; pp. 511-522.

Chinese language office action dated Jun. 20, 2022, issued in application No. TW 110130445.

* cited by examiner

PORTABLE ELECTRONIC DEVICE AND WOUND-SIZE MEASURING METHOD USING THE SAME

CROSS REFERENCE TO RELATED APPLICATIONS

This application claims priority of Taiwan Patent Application No. 110130445, filed on Aug. 18, 2021, the entirety of which is incorporated by reference herein.

BACKGROUND OF THE DISCLOSURE

Field of the Disclosure

The disclosure relates to image processing, and, in particular, to a portable electronic device and a wound-size measuring method using the same.

Description of the Related Art

Today's hospitals are prone to encounter many problems in the care of patients' wounds. For example, the types of wounds are diverse, and clinical staff are traditionally used to divide the professions, resulting fragmented wound records and databases in hospitals, and there is a lack of integrated care platforms that meet the needs of the market. In addition, the size records of wound photographs are complicated, and traditional methods have to rely on manual measurement with a ruler or with external hardware equipment, which is not convenient to application, and it is difficult to promote due to cost considerations. In addition, the patient's wound-care process needs to be continuous, but it is difficult to track and judge the condition of the patient's wound in the community long-term care base and in the patient's home, and there is a lack of continuous care by experts with professional experience dealing with wounds.

BRIEF SUMMARY OF THE DISCLOSURE

In view of the above, a portable electronic device and a wound-size measuring method are provided to solve the aforementioned problems.

In an exemplary embodiment, a portable electronic device is provided, which includes: an inertial-measurement unit, a camera device, a storage device, and a processor. The inertial-measurement unit is configured to detect a pitch angle of the portable electronic device. The camera device is configured to obtain an input image. The storage device is configured to store an operating system, a wound-measuring program, a CNN (convolutional neural network) model, and an RPN (regional proposal network) model. The processor is configured to perform the wound-size measuring program to perform the following steps: using the CNN model to recognize the input image, and selecting a part of the input image with the highest probability of containing a wound as an output wound image; and calculating an actual height and an actual width of the output wound image according to a lens-focal-length parameter reported by the operating system, a plurality of reference calibration parameters corresponding to the pitch angle, and a pixel-height ratio and a pixel-width ratio of the output wound image.

In some embodiments, the reference calibration parameters comprise a reference-object actual height, a reference-object actual width, a reference-object pixel-height ratio, and a reference-object focal distance.

In some embodiments, during a horizontal-calibration process of the wound-measuring program, the portable electronic device takes a picture of a reference object at the pitch angle of 0 degrees to obtain a first reference-object image, and obtains a first reference-object focal distance from an API (application programming interface) of the operating system, and the reference object has the reference-object actual height and the reference-object actual width. During a vertical-calibration process of the wound-measuring program, the portable electronic device takes another picture of the reference object at the pitch angle of 90 degrees to obtain a second reference-object image, and obtains a second reference-object focal distance from the API of the operating system. The processor divides a first pixel height of the first reference-object image displayed on a display panel of the portable electronic device by a second pixel height of the display panel to obtain a first reference-object pixel-height ratio or a second reference-object pixel-height ratio.

In some embodiments, in response to the pitch angle being between 0 and 45 degrees, the processor uses the first reference-object focal distance as the reference-object focal distance, and uses the first reference-object pixel-height ratio as the reference-object pixel-height ratio. In response to the pitch angle being between 45 and 90 degrees, the processor uses the second reference-object focal distance as the reference-object focal distance, and uses the second reference-object pixel-height ratio as the reference-object pixel-height ratio.

In some embodiments, the processor calculates equation (1) and equation (2) to obtain the actual height and the actual width of the output wound image, where equation (1) and equation (2) are expressed as follows:

$$h_m = h_c \times \frac{g_c \times p_m}{g_m \times p_c} \quad (1)$$

$$w_m = w_c \times \frac{g_c \times p_m}{g_m \times p_c} \quad (2)$$

where $h_c$ denotes the reference-object actual height; $g_c$ denotes the reference-object focal distance; $p_c$ denotes the reference-object pixel-height ratio; $h_m$ denotes the actual height of the output wound image; $g_m$ denotes the lens-focal-length parameter; $p_m$ denotes the pixel-height ratio; $w_m$ denotes the actual width of the output wound image; and we denotes the reference-object actual width.

In some embodiments, the processor further performs a machine-learning clustering algorithm to divide the output wound image into a wound region and a normal-skin region. The processor further calculates a first pixel number in the output wound image and a second pixel number in the wound region, and divides the second pixel number by the first pixel number to obtain a wound-region pixel ratio. The processor further multiplies the actual height of the output wound image by the actual width of the output wound image to obtain an actual area of the output wound image, and multiplies the actual area by the wound-region pixel ratio to obtain an actual area of the wound region.

In some embodiments, the processor further calculates a first red average, a first green average, and a first blue average of a red sub-pixel, a green sub-pixel, and a blue sub-pixel of each pixel in the wound region, and calculates a second red average, a second green average, and a second blue average of a red sub-pixel, a green sub-pixel, and a blue sub-pixel of each pixel in the normal-skin region. The processor calculates an Euclidean distance between the wound region and the normal-skin region to represent the severity of the wound region according to the first red average, the first green average, the first blue average, the second red average, the second green average, and the second blue average.

In some embodiments, in response to the processor determining that the actual area of the output wound image is larger than the actual area of a previous output wound image by a first predetermined ratio, the processor informs a server to add a username of the portable electronic device into a care list for medical staff to conduct related inspection.

In some embodiments, in response to the processor determining that the severity of the output wound image is greater than the severity of a previous output wound image by a second predetermined ratio, the processor informs a server to add a username of the portable electronic device into a care list for medical staff to conduct related inspections.

In some embodiments, before the processor uses the CNN model to recognize the input image, the processor uses the RPN model to generate a plurality of first bounding boxes using the input image, and filters out a plurality of second bounding boxes with probabilities of being a wound greater than a predetermined value from the first bounding boxes. The CNN model selects the second bounding box with the highest probability of being a wound as the output wound image.

In another exemplary embodiment, a wound-size measuring method, for use in a portable electronic device is provided. The portable electronic device comprises a display panel and a camera device. The method includes the following steps: obtaining an input image via the camera device; using a CNN (convolutional neural network) model to recognize the input image, and selecting a part of the input image with the highest probability of containing a wound as an output wound image; and calculating an actual height and an actual width of the output wound image according to a lens-focal-length parameter reported by an operating system running on the portable electronic device, a plurality of reference calibration parameters corresponding to a pitch angle of the portable electronic device, and a pixel-height ratio and a pixel-width ratio of the output wound image.

BRIEF DESCRIPTION OF THE DRAWINGS

The disclosure can be more fully understood by reading the subsequent detailed description and examples with references made to the accompanying drawings, wherein.

DETAILED DESCRIPTION OF THE DISCLOSURE

Figure 1:
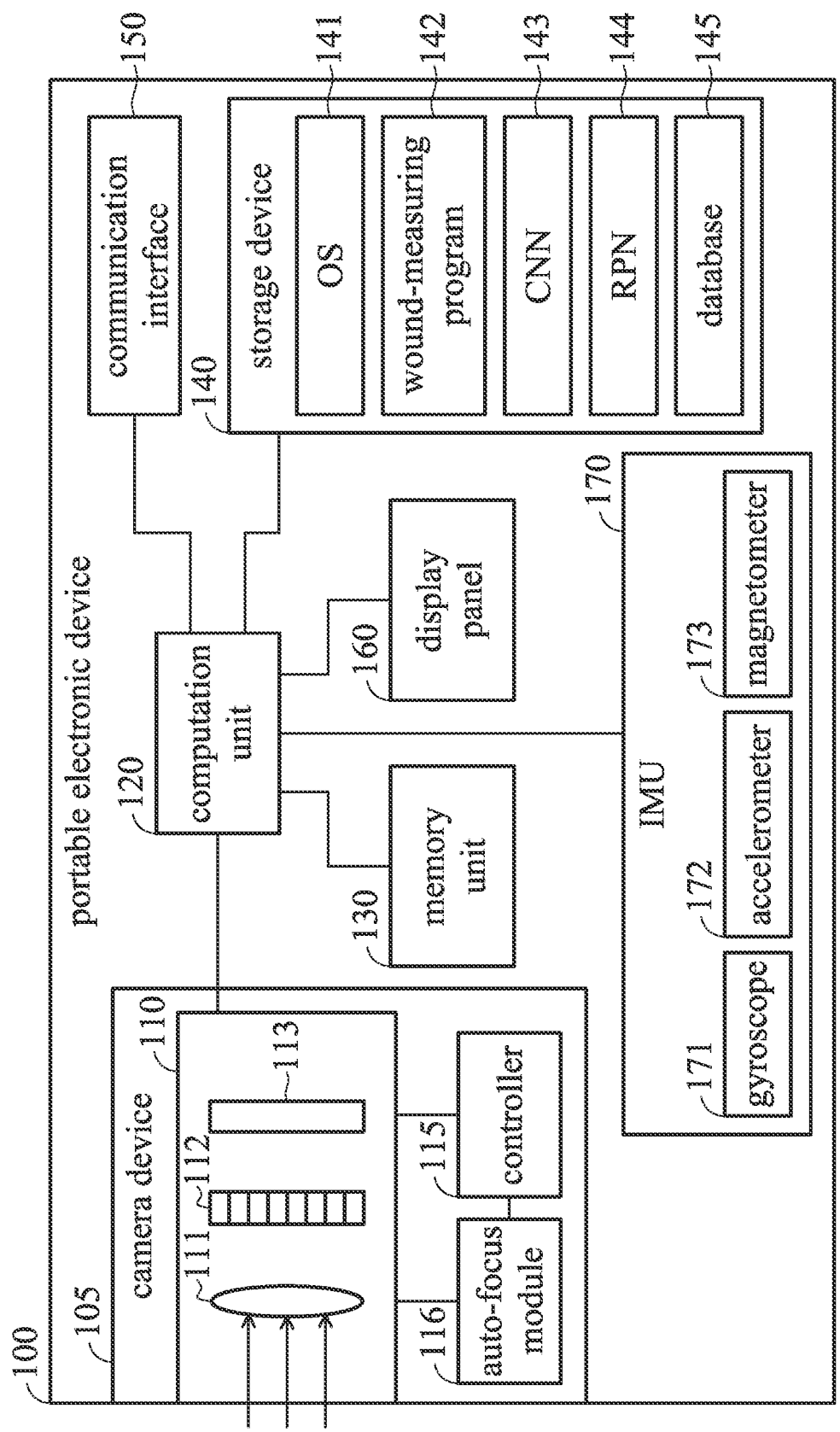
FIG. 1 is a block diagram of a portable electronic device in accordance with an embodiment of the disclosure.

The following description is made for the purpose of illustrating the general principles of the disclosure and should not be taken in a limiting sense. The scope of the disclosure is best determined by reference to the appended claims.

It is to be understood that the following disclosure provides one or more embodiments or examples to implement various features of the embodiments of the disclosure. The elements and arrangements of the specific examples disclose below are intended to simplify the embodiments of the disclosure and are not intended to be limited to the examples. In addition, the features in the drawings are not drawn to scale and are for illustrative purposes only.

FIG. 1 is a block diagram of a portable electronic device in accordance with an embodiment of the disclosure. The portable electronic device 100 may be a smartphone, a tablet PC, a laptop, etc., but the disclosure is not limited thereto. As depicted in FIG. 1, the portable electronic device 100 includes a camera device 105, a computation unit 120, a memory unit 130, a storage device 140, a communication interface 150, a display panel 160, and an inertial-measurement unit (IMU) 170. For example, the camera device 105 includes at least one camera module 110, a controller 115, and an auto-focus module 116.

The camera module 110 includes a lens 111, a color filter array (CFA) 112, and an image sensor 113. The color filter array 112 may include a plurality of red filters, green filters, and blue filters. The red, green, and blue filters may be arranged in a predetermined pattern such as a Bayer pattern or other types of patterns. The image sensor 113 may be a color image sensor that is implemented by a charge-coupled-device (CCD) sensor, or a complementary metal-oxide semiconductor (CMOS) sensor. The controller 115, for example, may be a microcontroller, but the disclosure is not limited thereto.

The incident light from the scene of the target object may pass through the lens 111 and the color filter array 112 to form an image on the image sensor 113, so that the photoelectric element of each pixel in the image sensor 113 may convert the sensed light into an electric signal that is transmitted to the controller 115. The controller 115 may transmit each pixel in the captured image to the computation unit 120. The auto-focus module 116, for example, may include a step motor that is configured to adjust the focal length of the lens 111 or the whole camera module 110 according to a control signal from the controller 115.

The controller 115, for example, may execute a passive auto-focus algorithm (e.g., a contrast-detection or phase-detection auto-focus algorithm) on the image captured by the image sensor 113 or receive a focus touch-control signal from the display panel 160 to control the auto-focus module 116 to fine-tune the position of the lens 111 or the whole camera module 110, so that the image sensor 113 can precisely focus on the target object to capture the object image. In addition, the controller 115 may transmit the focus information of the camera module 110 to the computation unit 120, wherein the focus information, for example, may be information about the focal length, steps of the step motor, etc., but the disclosure is not limited thereto.

In some embodiments, the portable electronic device 100 may include two or more camera modules 110, wherein the lenses 111 in different camera modules 110 may have different focal-length ranges, and the controller 115 may perform auto-focusing using the images captured by different camera modules 110 to control the auto-focus module 116 to fine-tune the lens 111 or the selected camera module 110 which has the corresponding focal-length range, so that the image sensor 113 in the selected module 110 may correctly focus on the target object. The controller 115 may also transmit the focus information about the camera module 110 selected by the auto-focusing function to the computation unit 120, wherein the focus information, for example, may be information about the focal length, the steps of the step motor, etc., but the disclosure is not limited thereto.

The computation unit 120 is electrically connected to the camera device 105. The computation unit 120 can be implemented in various ways, such as being implemented by a dedicated hardware circuit or general-purpose hardware (e.g., a single processor, multiple processors capable of performing parallel processing, or other processors having computation capability). For example, the aforementioned processor may be a central processing unit, a general-purpose processor, or a microcontroller, but the disclosure is not limited thereto.

The storage device 140, for example, may be a non-volatile memory such as a hard-disk drive, a solid-state disk, or a read-only memory, but the disclosure is not limited thereto. The storage device 140 is configured to store an operating system (OS) 141 (e.g., iOS or ANDROID operating systems) of the portable electronic device 100, a wound-measuring program 142, a convolutional neural network (CNN) model 143, and a regional-proposal network (RPN) model 144.

Assuming that the CNN model 143 and RPN model 144 have undergone the model-training process, the RPN model 144 can divide the object image (e.g., an input image) captured by the camera device 105 into a plurality of bounding boxes, and find one or more bounding boxes with a higher probability having a wound therein from the plurality of bounding boxes, and the one or more bounding boxes are input to the CNN model 143. The CNN model 143 may perform image recognition on each bounding box to obtain the bounding box having the highest probability (or confidence) having a wound therein as an output wound image. The wound-measuring program 142 may estimate dimension information of the output wound image according to a field of view (FoV) of the camera device 105 and a lens-focal-length parameter reported by the operating system 141, wherein the dimension information may be width and height of the target object.

The memory unit 130, for example, may be a volatile memory such as a static random access memory (SRAM) or a dynamic random access memory (DRAM), but the disclosure is not limited thereto. The memory unit 130 may be used as an execution space of the operating system 141, and a storage space of the temporarily stored intermediate data generated by the wound-measuring program 142, and an image buffer. For example, the computation unit 120 may load the operating system 141 and the wound-measuring program 142 stored in the storage device 140 to the memory unit 130 for execution. The communication interface 150, for example, may include wired and/or wireless transmission interfaces that are configured to connect the portable electronic device 100 to other electronic devices or servers.

The display panel 160, for example, may be a liquid-crystal display panel, a light-emitting diode (LED) display panel, an organic light-emitting diode (OLED) display panel, e-Ink, etc., but the disclosure is not limited thereto. In some embodiments, a touch-control device (not shown) can be integrated into the display panel 160 for performing touch operations. The touch device may be a capacitive or resistive touch-control device, and the display panel 160 can be regarded as a "touch panel", but the disclosure is not limited thereto.

The inertial-measurement unit 170 may include a gyroscope 171, an accelerometer 172, and a magnetometer 173. The gyroscope 171 is configured to measure the orientation and angular speed of the portable electronic device 100. The accelerometer 172 is configured to measure the acceleration of the portable electronic device 100, and the magnetometer 173 is configured to measure the magnetic strength and direction at the position where the portable electronic device 100 is located. The data measured by the gyroscope 171, accelerometer 172, and magnetometer 173 can be collectively regarded as inertial information. For example, the accelerometer 172 and magnetometer 173 of the inertial-measurement unit 170 may detect the pitch of the portable electronic device 100.

In an embodiment, the operating system 141 running on the portable electronic device 100, for example, may be the Android operating system. After the auto-focusing procedure, the lens-focal-length parameter reported by an application program interface (API) of the operating system 141 may be LENS_FOCUS_DISTANCE or LENS_INFO_FOCUS_DISTANCE_CALIBRATION. For example, the aforementioned lens-focal-length parameter is a value calibrated by the API of the operating system 141, and its unit is diopter=1/meter. The value of 0 indicates the farthest distance that the lens 111 can focus, but the farthest distance is not expressed as infinity. For example, when then distance between the target object and the lens 111 is in a specific focal-length range (e.g., about 10 to 25 cm) and the tilt angle of the portable electronic device 100 is at a specific angle (e.g., 0 degrees or 90 degrees), the focal length f used by the lens 111 can be calculated using equation (1):

$$f = \frac{1}{\text{LENS\_INFO\_FOCUS\_DISTANCE\_CALIBRATION}} \quad (1)$$

It should be noted that the value of the lens-focal-length parameter LENS_FOCUS_DISTANCE or LENS_INFO_FOCUS_DISTANCE_CALIBRATION reported by the operating system 141 will also change with the pitch angle of the portable electronic device 100.

In another embodiment, if the portable electronic device 100 is a model of the iPhone 4S or above and the operating system 141 is a version of iOS 8 or above, the lens-focal-length parameter reported by the operating system 141, for example, may be "lensPosition". The lens-focal-length parameter lensPosition may be a value between 0 and 1, where the value 0 may indicate the closest distance that the lens 111 can focus on, and the value 1 may indicate the farthest distance that the lens 111 can focus on, but the farthest distance does not represent infinity. It should be noted that the lens-focal-length parameter lensPosition does not directly indicate the focal length value of the lens 111, but a value that has been converted by the operating system 141 and is not equal to the value of a constant divided by the focal length. In addition, the value of the lens-focal-length parameter lensPosition reported by the operating system 141 also changes according to the pitch angle of the portable electronic device 100.

Figure 2A:
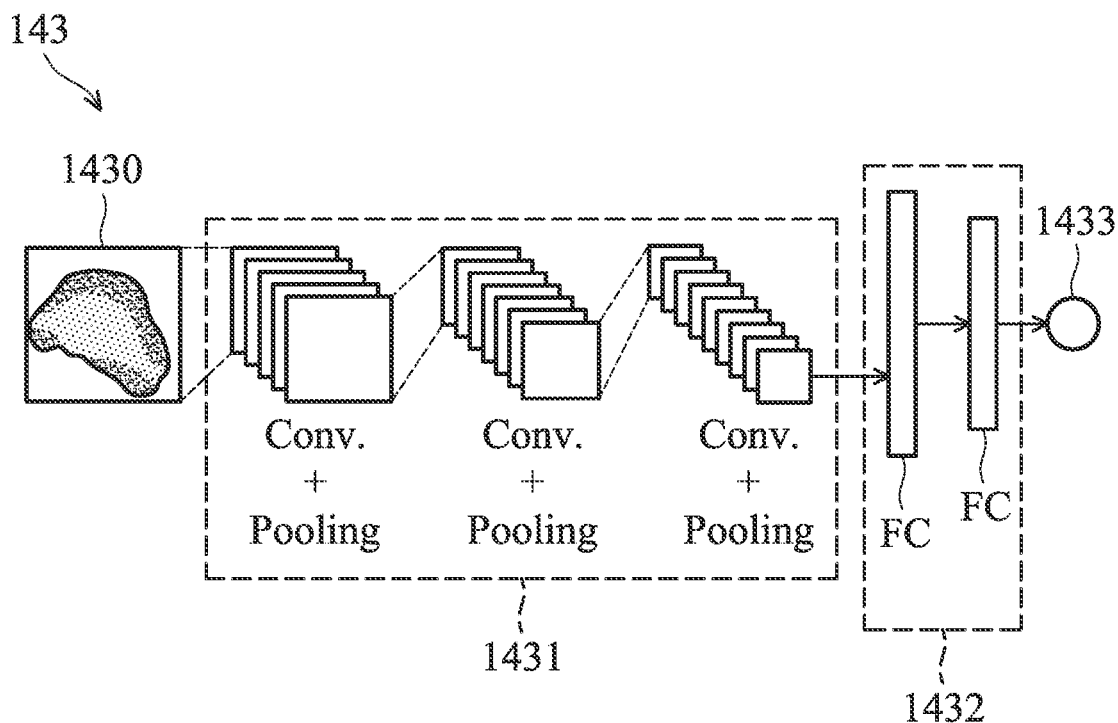
FIG. 2A is a diagram of the model-training procedure of a CNN model in accordance with an embodiment of the disclosure.

FIG. 2A is a diagram of the model-training procedure of a CNN model in accordance with an embodiment of the disclosure.

In an embodiment, during the model-training procedure, medical professionals can first mark the wound images in each training image (meaning that the area of the wound image is less than or equal to each training image), and each wound image is integrated into a feature-data set. The model-training procedure of the CNN model 143 and the RPN model 144, for example, can use the same feature-data set to train the CNN model 143 and the RPN model 144 at the same time. In some embodiments, the CNN model 143 and the RPN model 144 can be implemented using Unet, Faster R-CNN, or Mask R-CNN models, but the disclosure is not limited thereto.

The aforementioned feature-data set may include wound images of chronic wounds or acute wound of patients. Chronic wounds can include diabetic foot ulcers, bedsores or pressure ulcers, venous ulcers, and so on. Acute wounds may include chronic poorly healed pressure sores, hemangioma, ulcers, burns, and scalds, infections and necrosis of diabetic feet and toes, etc., but the disclosure is not limited thereto. It should be noted that that because the same feature-data set is used for model training, the CNN model 143 and the RPN model 144 can use a common feature map.

For example, during the model-training process, a wound image (e.g., the wounded part) marked by a medical professional is used as the input image 1430 of the CNN model 143. The CNN model 143 can also be called a wound-recognition model, and it includes a feature map 1431 and a network layer 1432. The feature map 1431 can be, for example, multiple sets of convolutional layers (Cony) and max pooling (e.g., a pooling layer, abbreviated as MaxPool). For example, the convolutional layer can perform convolution operations on the input image 1430 and extract features from the input image 1430, and the pooling layer can amplify the extracted features. The advantage of using the pooling layer is that when the input image has a shift of several pixels, it will not affect the recognition result of the CNN model 143, and it has a good anti-noise function. Finally, the CNN model 143 flattens the feature-extraction results to input to the network layer 1432. The network layer 1432 includes, for example, at least two full connection layers (abbreviated as "FC"). After the flattened feature-extraction result passes through the network layer 1432, the output wound image 1433 and its corresponding confidence level are obtained.

In some embodiments, in order to reduce the problem of over-fitting of the CNN model 143, weighting factors of some layers in the CNN model 143 (e.g., a fully-connected layer or a convolution layer) can be randomly and continuously updated during the model-training procedure. In addition, a data-augmentation function can also be added in the model-training procedure to greatly increase the amount of training data. For example, the computation unit 120 may execute a training-data enhancement program (not shown) to mirror each wound image in the feature-data set, to rotate each wound image by 0, 90, 180, or 270 degrees, to scaling up/down each wound image, and to adjust contrast and exposure of each wound image to obtain different enhanced training data. The model-training procedure uses the aforementioned enhanced training data to train the CNN model 143, and the training is completed when the CNN model 143 is trained to converge.

Figure 2B:
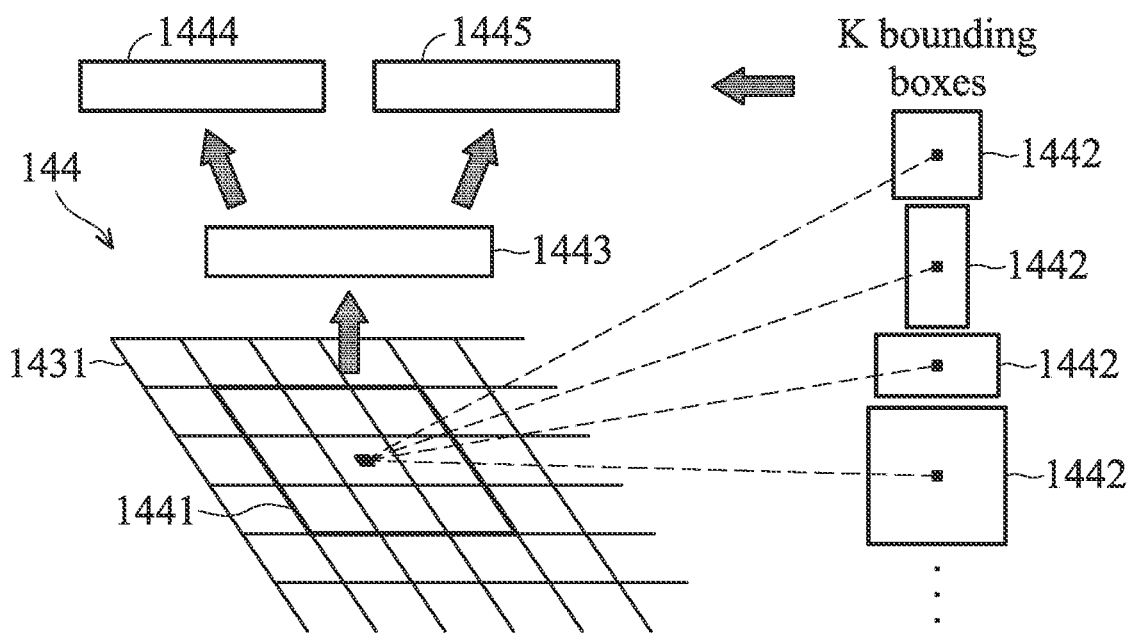
FIG. 2B is a diagram of the architecture of the RPN model in accordance with an embodiment of the disclosure.

FIG. 2B is a diagram of the architecture of the RPN model in accordance with an embodiment of the disclosure.

The RPN model 144 can also be referred to as a wound-locating model, and its model architecture is shown in FIG. 2B. In an embodiment, the input of the RPN model 144 is a feature map (e.g., abbreviated as "cony feature map") 1431 of CNN model 143. In another embodiment, the RPN model 144 may include a separate feature map (not shown), which is different from the feature map 1431 of the CNN model 143. In addition, during the model-training procedure of the RPN model 144, the input of the feature map of the RPN model 144 is an image that has not been cropped but has been manually marked with the location of the wound, which means that each training image has been marked in the training-data set.

For ease of description, the input of the RPN model 144 in FIG. 2B is the feature map 1431 of the CNN model 143. For example, the RPN model 144 takes a sliding window 1411 (e.g., a 3×3 convolutional layer) on the feature map 1431, and then uses k different anchor boxes 1442 corresponding to each pixel to calculate the probability that each anchor box includes an object. For example, an intermediate layer 1443 having 256 dimensions can be calculated, and a classification layer 1444 and a regression layer 1445 corresponding to each sliding window 1441 can be obtained, wherein the classification layer 1444 has 2 k scores, and the regression layer 1445 has 4 k coordinate positions. The RPN model 144 can obtain the bounding box most likely to contain the object according to the corresponding score of each sliding window 1441.

Figure 2C:
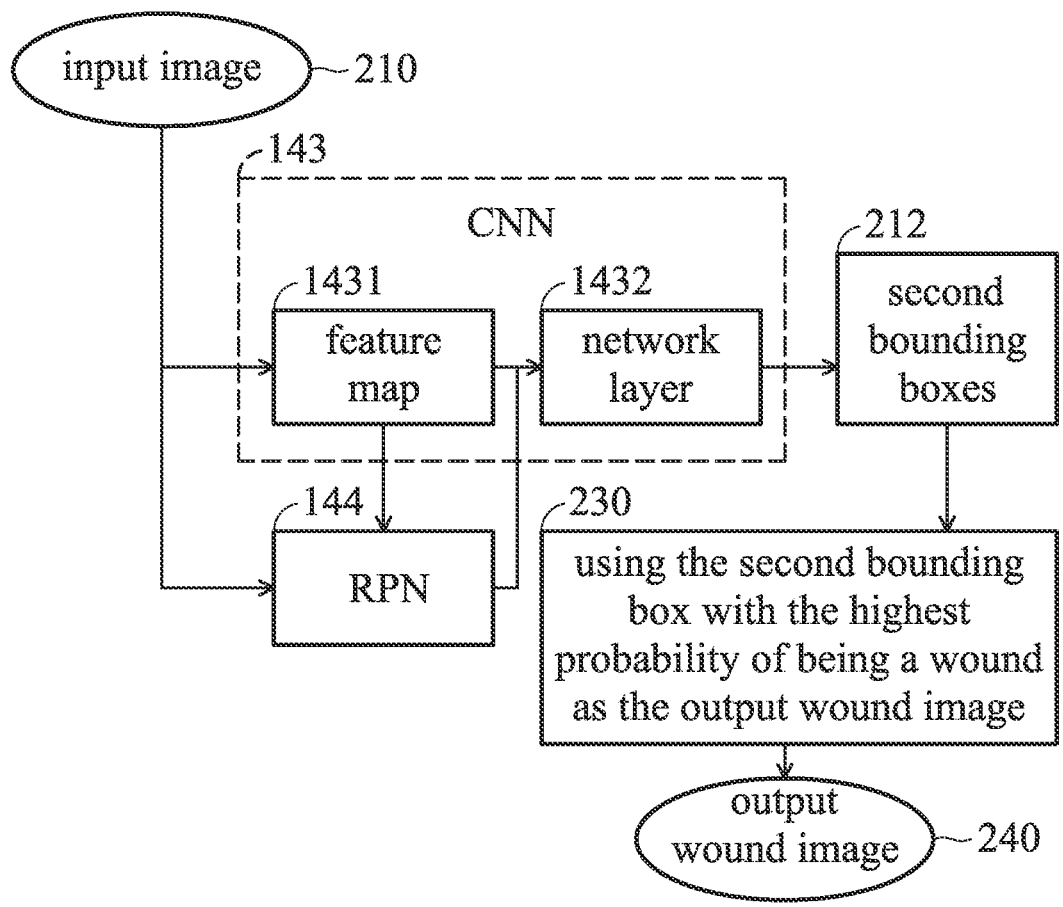
FIG. 2C is a flow chart of wound recognition using the CNN model and the RPN model in accordance with an embodiment of the disclosure.
Figure 2D:
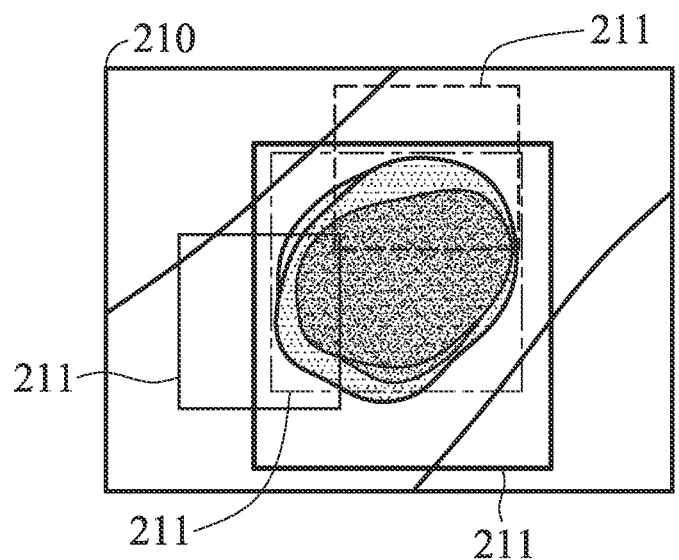
FIG. 2D is a diagram of dividing the input image into a plurality of first bounding boxes using the RPN model in accordance with the embodiment of FIG. 2C.
Figure 2E:
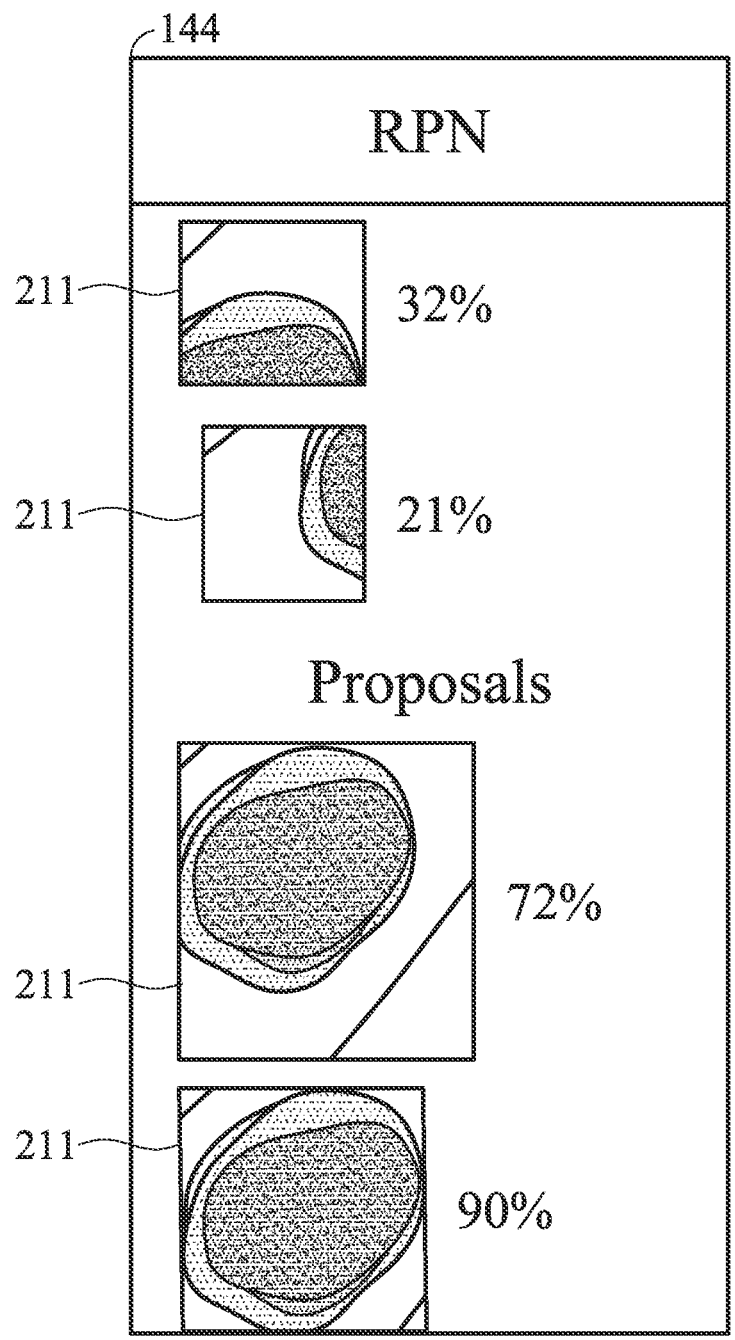
FIG. 2E is a diagram of determining a plurality of second bounding boxes from the first bounding boxes in accordance with an embodiment of FIG. 2C.
Figure 2F:
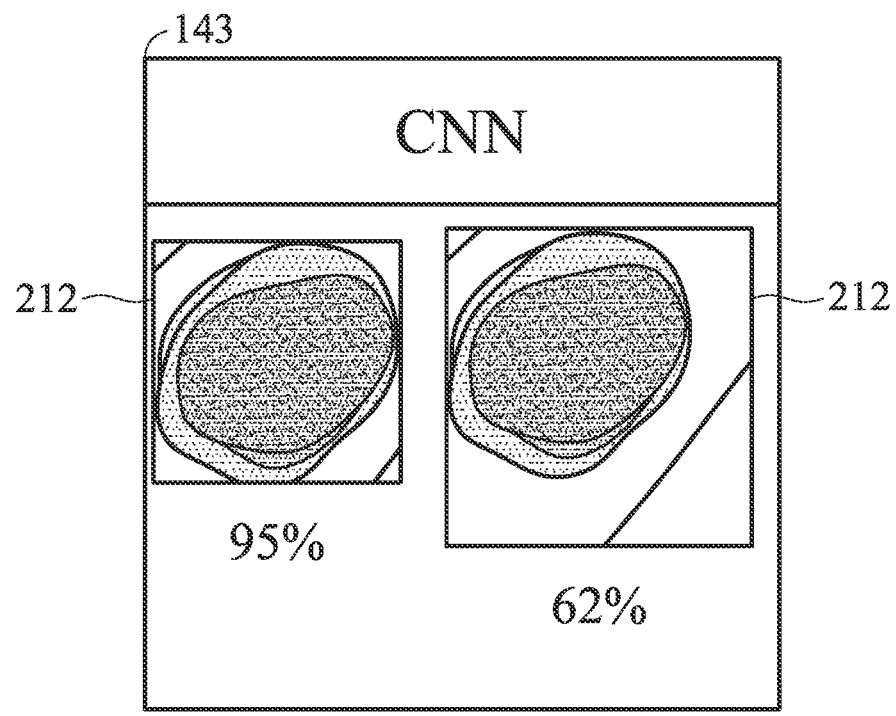
FIG. 2F is a diagram of using a CNN model to determine the probability that each second bounding box includes a wound in accordance with the embodiment of FIG. 2C.
Figure 2G:
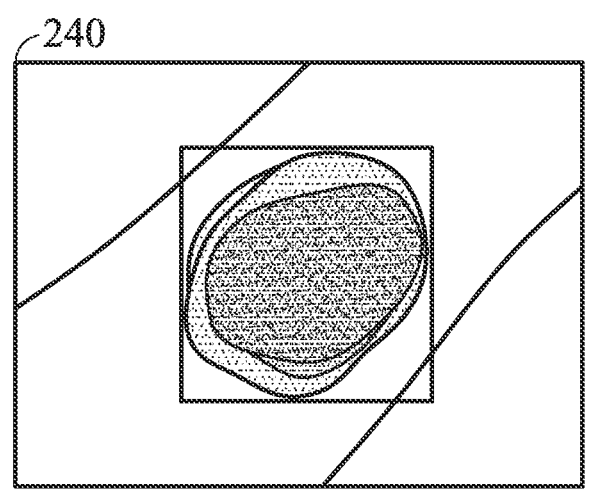
FIG. 2G is a diagram of the output wound image in accordance with an embodiment of FIG. 2C.

FIG. 2C is a flow chart of wound recognition using the CNN model and the RPN model in accordance with an embodiment of the disclosure. FIG. 2D is a diagram of dividing the input image into a plurality of first bounding boxes using the RPN model in accordance with the embodiment of FIG. 2C. FIG. 2E is a diagram of determining a plurality of second bounding boxes from the first bounding boxes in accordance with an embodiment of FIG. 2C. FIG. 2F is a diagram of using a CNN model to determine the probability that each second bounding box includes a wound in accordance with the embodiment of FIG. 2C. FIG. 2G is a diagram of the output wound image in accordance with an embodiment of FIG. 2C.

Please refer to FIGS. 2C to 2G. In the image-recognition phase, the input image 210 is subjected to feature extraction of the CNN model 143 to obtain a feature map 1431, and the RPN model 144 can divide the input image 210 into a plurality of first bounding boxes 211 according to the feature map 1431, as shown in FIG. 2D, where the probability that each first bounding box 211 from top to bottom contains a wound is 32%, 21%, 72%, and 90%, respectively.

The RPN model 144 filters out a plurality of second bounding boxes 212 with a higher probability to contain a wound therein from the first bounding boxes 211. For example, the RPN model 144 can set a threshold probability. If the probability that the first bounding box 211 contains a wound is greater than the threshold probability, the RPN model 144 puts the first bounding box 211 into the proposals, where the first bounding boxes 211 in the proposals can be regarded as the second bounding boxes 212, as shown in FIG. 2E.

The RPN model 144 may input each second bounding box 212 into the network layer 1432 of the CNN model 143 to obtain the probability whether the image of each second bounding box 212 is a wound, as shown in FIG. 2F, where the probability that each second bounding box 212 from left to right contains a wound is 95% and 62%, respectively. Finally, at block 230, the CNN model 143 uses the second bounding box 212 with the highest probability (e.g., 95%, which can also be called as the confidence level) that contains a wound as the output wound image 240, and display the output wound image 240 on the display panel 160, as shown in FIG. 2G. Specifically, because the RPN model 144 can first find the plurality of second bounding boxes 212 with the highest probability of containing a wound from the input image, and the CNN model 143 can determine the probability that each second bounding box contains a wound, so the CNN model 143 with the RPN model 144 can increase the calculation speed of the portable electronic device 100 to determine whether the input image is a wound image, and can increase the accuracy of wound recognition.

Figure 4A:
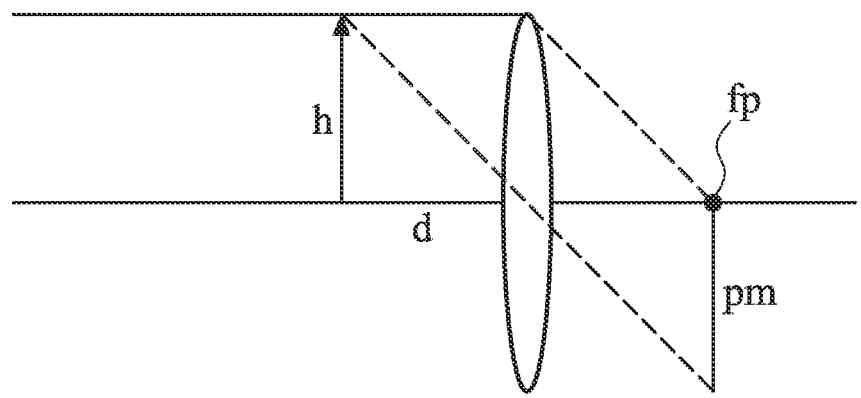
FIGS. 4A and 4B are diagrams of imaging at different distances by a camera device in accordance with an embodiment of the disclosure.
Figure 4B:
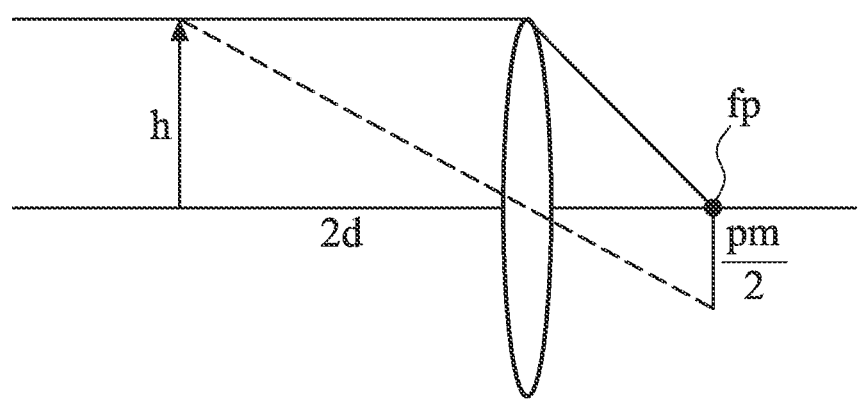

FIGS. 4A and 4B are diagrams of imaging at different distances by a camera device in accordance with an embodiment of the disclosure.

In an embodiment, the wound-measuring problem 142 can calculate the distance d of the object to be measured according to equation (2):

$$d = \frac{f \times h \times p_w}{p_m \times s} \quad (2)$$

where h denotes the actual height of the object; f denotes the focal length of the camera device 105; $p_w$ denotes the number of pixels of the image height; $p_m$ denotes the number of pixels occupied by the target object in the image height; s denotes the length of the photosensitive element. Because most of the lenses 111 of the portable electronic device 100 currently on the market are fixed-focus lenses, the focal length f, the image height $p_w$, and the length s of the photosensitive element can be regarded as fixed values, and these three parameters can be simplified as a lens parameter p, as shown in equation (3):

$$p = \frac{f \times p_w}{s} \quad (3)$$

However, when the wound-measuring program 142 is calculating the wound size in the output wound image, the object distance d (i.e., the distance between the camera device 105 and the target object (wound)) and the actual height h of the target object are both unknown, the wound-measuring program 142 may calculate the distance d of the target object using the lens-focal-length parameter g. For example, the lens-focal-length parameter g has a reciprocal relationship with the object distance d, but the value of the lens-focal-length parameter g after reciprocal conversion is not equal to the object distance d, and the reciprocal of the lens-focal-length parameter g needs to be multiplied by the shift offset w to obtain the object distance, as shown in equation (4):

$$d = \frac{1}{g} \times w \quad (4)$$

As depicted in FIG. 4A, assuming that the actual height of the target object (e.g., a wound) is fixed at h and the object distance is d, the reflected light of the target object passes through the focus fp on the display panel 160 of the portable electronic device 100 to form a first display screen on the display panel 160, and the first display screen has an imaging height $p_m$. As depicted in FIG. 4B, if the object distance is increased to 2d, the reflected light of the target object passes through the focus fp on the display panel 160 of the portable electronic device 100 to form a second display screen on the display panel 160, and the second display screen has an imaging height of $$\frac{p_m}{2}.$$

Therefore, according to equations (2) and (3), the proportional relation of equation (5) can be obtained as follows:

$$1 = \frac{h}{d \times p_m} \times p \quad (5)$$

Similarly, according to equation (5), when the object distance d is fixed, if the height of the target object is 2h and h, the imaging height of the display screen is $2p_m$ and $p_m$, respectively. In addition, according to equation (5), when the height of the target object is fixed at h and the object distance is d and 2d, the imaging height of the display screen is $p_m$ and $p_m/2$, respectively.

When the computation unit 120 executes the wound-measuring program 142 for the first time, the wound-measuring program 142 can enter a calibration mode. In the calibration mode, the computation unit 120 may turn on the camera device to focus on a reference object of a known size and take a picture, and the user can frame the range of the reference object on the display panel 160, so the computation unit 120 can get a reference value of the focal distance and a height of the reference object. Then, according to equation (4), combined with the known ratio of the reference object, equation (6) can be obtained as follows:

$$\frac{h_c \times g_c}{w \times p_c} \times p = \frac{h_m \times g_m}{w \times p_m} \times p \quad (6)$$

where $h_c$ denotes the reference-object actual height; $g_c$ denotes the reference-object focal distance; $p_c$ denotes the reference-object pixel-height ratio; $h_m$ denotes the target-object actual height; $g_m$ denotes the target-object focal distance; $p_m$ denotes the target-object pixel-height ratio. In some embodiments, the reference object, for example, may be a health-insurance card or an ID card, or other objects with a fixed and known size.

Equation (6) can be simplified to obtain equation (7) to obtain the actual height of the target object, where equation (7) is shown as follows:

$$h_m = h_c \times \frac{g_c \times p_m}{g_m \times p_c} \tag{7}$$

For example, the size of the health-insurance card is 53.5 mm (width)*85.5 mm (height), therefore, the actual height $h_c$ of the reference object in equation (7) is a known value. In addition, the portable electronic device 100 uses the step motor of the auto-focus module 116 to adjust the position of the lens 111. However, the step motor is affected by the gravity of the earth, so the lens-focal-length parameters reported by the operating system 141 will be different when the pitch angle of the portable electronic device 100 is 0 degrees and 90 degrees. It should be noted that equation (7) is used to calculate the actual height $h_m$ of the target object. If equation (7) is to be used to calculate the actual width $w_m$ of the target object, the actual height $h_m$ of the target object and the actual height $h_c$ of the reference object can be replaced with the actual width $w_m$ of the target object and the actual height we of the reference object, as shown in equation (8):

$$w_m = w_c \times \frac{g_c \times p_m}{g_m \times p_c} \tag{8}$$

The reference-object pixel-width ratio and the target-object pixel-width ratio object are similar to the reference-object pixel-height ratio $p_c$ and the target-object pixel-height ratio $p_m$, and thus the reference-object pixel-height ratio $p_c$ and the target-object pixel-height ratio $p_m$ can be directly used in equation (8). In some embodiments, the computation unit 120 may additionally calculate the reference-object pixel-width ratio $r_c$ and the target-object pixel-width ratio $r_m$ to replace the reference-object pixel-height ratio $p_c$ and the target-object pixel-height ratio $p_m$ in equation (8), respectively.

Figure 3A:
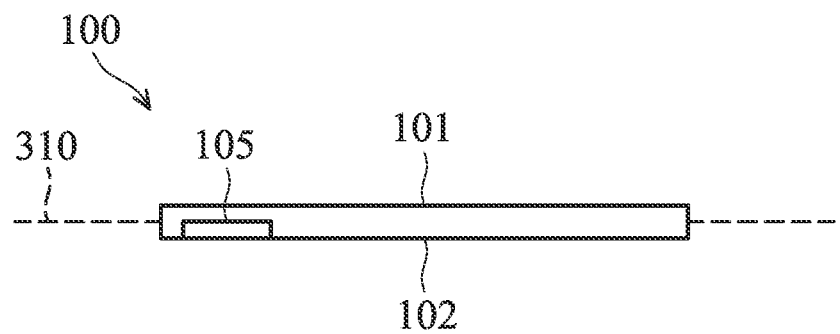
FIG. 3A is a diagram of the portable electronic device at the pitch angle of 0 degrees in accordance with an embodiment of the disclosure.

For example, when the front surface 101 and the rear surface 102 of the portable electronic device 100 are completely parallel to the horizontal line 310, the inertial-measurement unit 170 may detect that the pitch angle of the portable electronic device 100 is 0 degree, as shown in FIG. 3A.

Figure 3B:
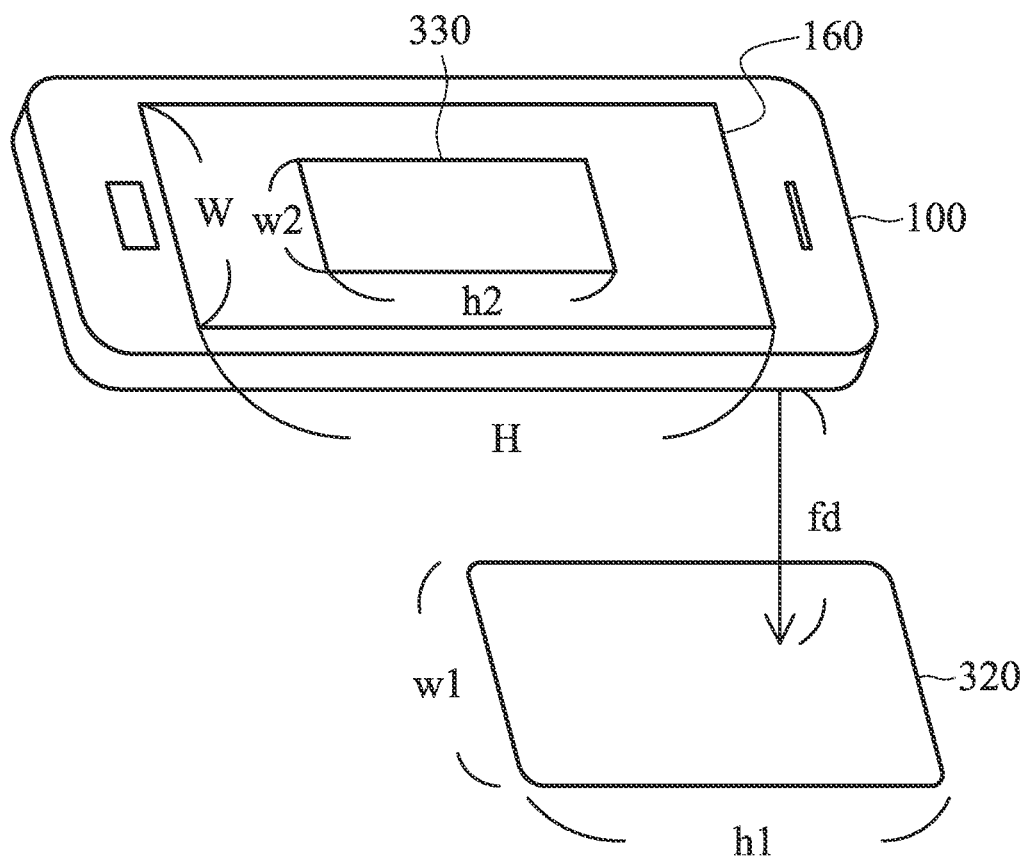
FIG. 3B is a diagram of the horizontal-calibration process of the portable electronic device in accordance with an embodiment of the disclosure.

The horizontal-calibration process of the portable electronic device 100 is shown in FIG. 3B. The user may use the portable electronic device 100 to capture the reference object 320 at a pitch angle of 0 degrees and a predetermined distance fd (e.g., between 10 to 15 cm) to obtain a reference-object image 330, wherein the height and width of the reference object 320 are h1 and w1 that correspond to the actual height $h_c$ of the reference object 320 and the actual width we of the reference object 320, respectively. The user can observe through the display panel 160 whether the captured reference-object image is clear, and can press the camera button to capture the reference-object image 330. The user can also adjust the frame on the display panel 160 to indicate the size range of the reference-object image 330, and save the calibration parameters.

For example, the resolution of the display panel 160 is W (pixel width)*H (pixel height), and the reference-object image 330 displayed on the display panel 160 has a pixel height h2 and a pixel width w2. If the pixel height h2 of the reference object image 330 is 1344 pixels, and the pixel height of the display panel 160 is 1920 pixels, the computation unit 120 can calculate the reference-object pixel-height ratio $p_c$=0.70. Meanwhile, if the aforementioned predetermined distance is about 13 cm, the lens-focal-length parameter reported by the API of the operating system 141 may be 7.59, and thus the computation unit 120 may set the reference-object focal distance $g_c$ to 7.59. Accordingly, a plurality of reference calibration parameters can be obtained during the horizontal-calibration process, such as the reference-object actual height $h_c$, reference-object pixel-height ratio $p_c$, and reference-object focal distance $g_c$.

Figure 3D:
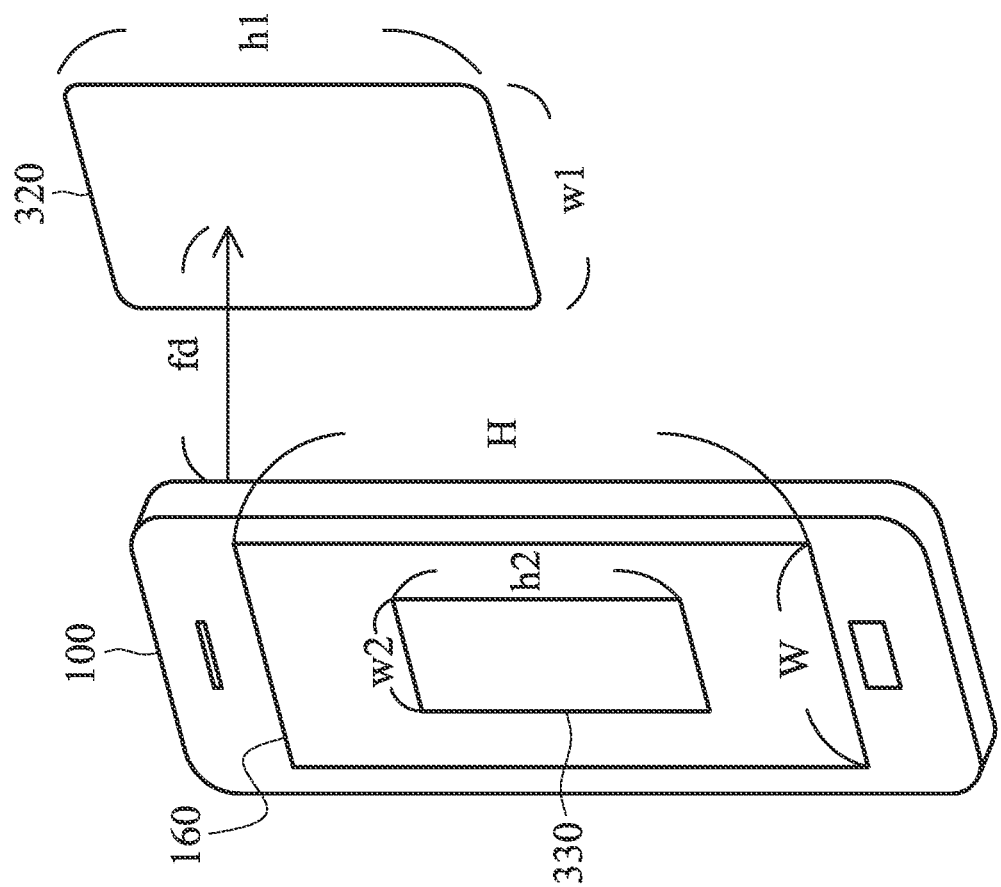
FIG. 3D is a diagram of the vertical-calibration process of the portable electronic device in accordance with an embodiment of the disclosure.
Figure 3C:
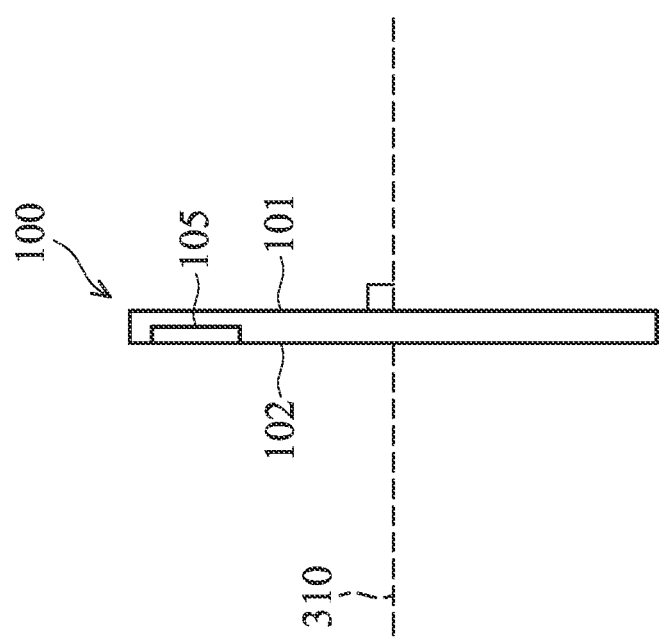
FIG. 3C is a diagram of the portable electronic device at the pitch angle of 90 degrees in accordance with an embodiment of the disclosure.

When the front surface 101 and the rear surface 102 of the portable electronic device 100 are perpendicular to the horizontal line 310, the inertial-measurement unit 170 may detect that the pitch angle of the portable electronic device 100 is 90 degrees, as shown in FIG. 3C.

The vertical-calibration process of the portable electronic device 100 is shown in FIG. 3D. The user may use the portable electronic device 100 to capture the reference object 320 at a pitch angle of 90 degrees and a predetermined distance fd (e.g., between 10 to 15 cm) to obtain a reference-object image 330, wherein the height and width of the reference object 320 are h1 and w1 that correspond to the actual height $h_c$ of the reference object 320 and the actual width we of the reference object 320, respectively. In addition, the resolution of the display panel 160 is W (pixel width)*H (pixel height), and the reference-object image 330 displayed on the display panel 160 has a pixel height h2 and a pixel width w2.

For example, if the pixel height h2 of the reference object image 330 is 1382 pixels, and the pixel height of the display panel 160 is 1920 pixels, the computation unit 120 can calculate the reference-object pixel-height ratio $p_c$=0.72. Meanwhile, if the aforementioned predetermined distance is about 13 cm, the lens-focal-length parameter reported by the API of the operating system 141 may be 8.65, and thus the computation unit 120 may set the reference-object focal distance $g_c$ to 8.65. Accordingly, a plurality of reference calibration parameters can be obtained during the vertical-calibration process, such as the reference-object actual height $h_c$, reference-object pixel-height ratio $p_c$, and reference-object focal distance $g_c$.

It should be noted that the reference-object focal distances $g_c$ obtained in the horizontal-calibration process and the vertical-calibration process are different reference calibration parameters. For example, when the pitch angle of the portable electronic device 100 is between 0 degrees and 45 degrees, the wound-measuring program 142 may use the reference calibration parameters obtained in the horizontal-calibration process to be used in equation (7) and equation (8) to calculate the target-object actual height $h_m$ and target-object actual width $w_m$ (e.g., expressed in centimeters). When the pitch angle of the portable electronic device 100 is greater than or equal to 45 degrees or is between 45 to 90 degrees, the wound-measuring program 142 may use the reference calibration parameters obtained in the vertical-calibration process to be used in equation (7) and equation (8) to calculate the target-object actual height $h_m$ and target-object actual width $w_m$ (e.g., expressed in centimeters).

Figure 5A:
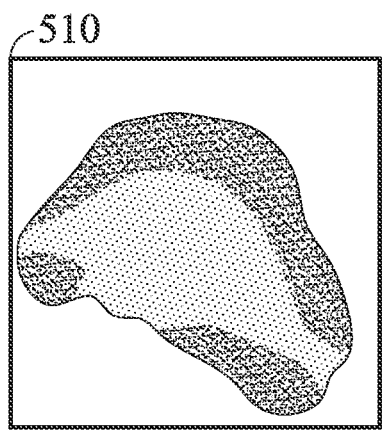
FIGS. 5A to 5C are diagram of grouping output wound images according to an embodiment of the disclosure.
Figure 5B:
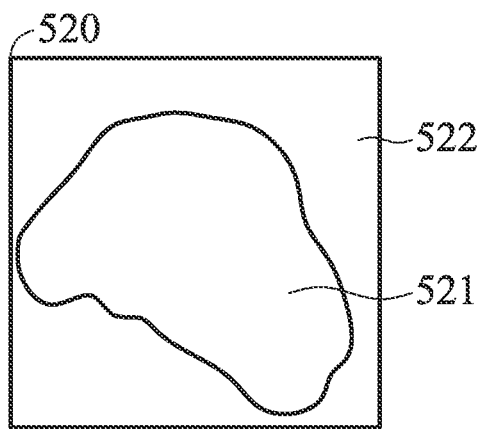
Figure 5C:
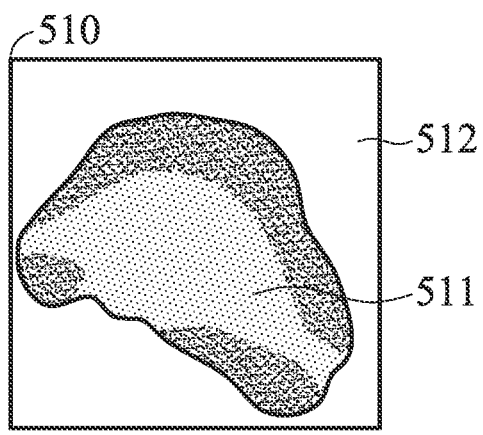

FIGS. 5A to 5C are diagram of grouping output wound images according to an embodiment of the disclosure.

FIG. 5A shows an output wound image 510 generated by the CNN model 143 and the RPN model 144, where the output wound image 510 may be an RGB image, which means that each pixel of the output wound image is composed of a red sub-pixel, a green sub-pixel, and a blue sub-pixel with a brightness between 0 and 255. The wound-measuring program 142 may use a machine-learning clustering algorithm to group each pixel of the output wound image 510, for example, it can be divided into a wound group and a normal-skin group. The aforementioned machine-learning grouping algorithm may be K-Means clustering method, hierarchical clustering method, or other clustering algorithms in the field of the present disclosure, but the disclosure is not limited thereto. For example, after the output wound image 510 in FIG. 5A is processed by the image-clustering process, a clustered image 520 shown in FIG. 5B can be obtained, which can be divided into a wound region 521 and a normal-skin region 522.

After the wound-measuring program 142 has obtained the wound region 521 and the normal-skin region 522 from the clustered image 520, the wound-measuring program 142 may calculate the area of the wound region 521 in the clustered image 520. For example, in the aforementioned embodiments, the wound-measuring program 142 may calculate the target-object actual height and the target-object actual width in the output wound image. Assuming that the target-object actual height and the target-object actual width are respectively 3 cm and 4 cm, the actual area corresponding to the output wound image 510 is 12 square centimeters. If the output wound image 510 has 50,000 pixels and the wound-measuring program 142 has calculated that there are 45,000 pixels in the wound region 521, the wound-measuring program 142 can calculate the wound-region pixel ratio is 45000/50000=0.9. Accordingly, the wound-measuring program 142 can calculate the actual area corresponding to the wound region 521 is 12*(45000/50000)=10.8 square centimeters.

In an embodiment, when the wound-measuring program 142 obtains information about the wound region 521 and the normal-skin region 522, the wound-measuring program 142 may divide the output wound image 510 into the a wound region 511 and a normal-skin region 512, and can know the pixel values of the red sub-pixel, green sub-pixel, and blue sub-pixel of each pixel in the wound region 511 and the normal-skin region 512, as shown in FIG. 5C. The wound-measuring program 142 may calculate average values for the red sub-pixel, green sub-pixel, and blue sub-pixel of each pixel in the wound region 521, where the average values for the red sub-pixels, green sub-pixels, and blue sub-pixels can be expressed by $W\_R_{avg}$, $W\_G_{avg}$, and $W\_B_{avg}$, respectively. The wound-measuring program 142 may calculate average values for the red sub-pixel, green sub-pixel, and blue sub-pixel of each pixel in the normal-skin region 522, where the average values for the red sub-pixels, green sub-pixels, and blue sub-pixels can be expressed by $N\_R_{avg}$, $N\_G_{avg}$, and $N\_B_{avg}$, respectively.

Afterwards, the wound-measuring program 142 may calculate severity of the wound region 521, where the severity can be calculated using equation (9):

$$\text{severity} = \sqrt{(N\_R_{avg} - W\_R_{avg})^2 + (N\_G_{avg} - W\_G_{avg})^2 + (N\_B_{avg} - W\_B_{avg})^2} \quad (9)$$

wherein $N\_R_{avg}$ denotes the average of all red sub-pixels in the normal-skin region 522; $N\_G_{avg}$ denotes the average of all green sub-pixels in the normal-skin region 522; $N\_B_{avg}$ denotes the average of all blue sub-pixels in the normal-skin region 522; $W\_R_{avg}$ denotes the average of all red sub-pixels in the wound region 521; $W\_G_{avg}$ denotes the average of all green sub-pixels in the wound region 521; $W\_B_{avg}$ denotes the average of all blue sub-pixels in the wound region 521.

The Euclidean distance that represents the severity may be a floating point number between 0 and 255. If the severity is closer to 255, it means that the severity of the wound region 521 is higher in comparison with the normal-skin region 522 (i.e., lower similarity between the wound region 521 and normal-skin region 522). If the severity is closer to 0, it means that the severity of the wound region 521 is lower in comparison with the normal-skin region 522 (i.e., higher similarity between the wound region 521 and normal-skin region 522).

Figure 6:
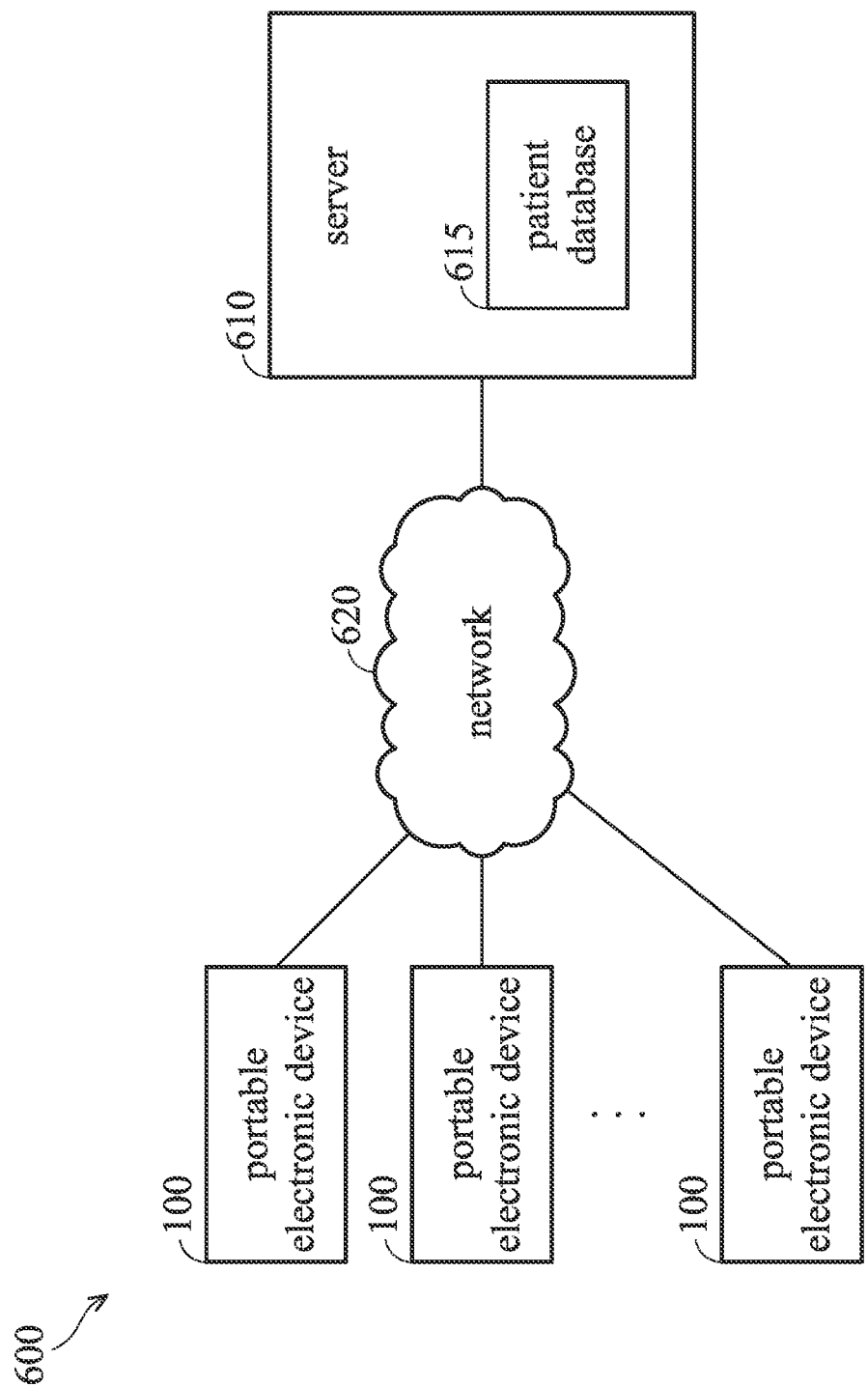
FIG. 6 is a block diagram of a wound-care system in accordance with an embodiment of the disclosure.

FIG. 6 is a block diagram of a wound-care system in accordance with an embodiment of the disclosure. Please refer to FIG. 1 and FIG. 6.

In an embodiment, the wound-care system 600 may include one or more portable electronic devices 100 and a server 610, wherein each portable electronic device 100 can be connected to the server 610 through a network 620. The patient or the medical staff can periodically use the corresponding portable electronic device 100 to take pictures of the wound of the patient to obtain an input image. The wound-measuring program 142 executed by each portable electronic device 100 can use the CNN model 143 and the RPN model 144 to recognize the input image to obtain the output wound image (i.e., the bounding box having the highest probability of being a wound cut from the input image).

Whenever a patient or a medical staff users the portable electronic device 100 to take a picture of the patient's wound, the wound-measuring program 142 can save the following data in a database 145 for use by subsequent care procedures, where the data may include as the output wound image generated by the CNN model 143 and the RPN model 144 and its time information (e.g., the shooting time of the input image) and size information (e.g., including height, width, and area), and severity of the wound region in the output wound image in comparison with the normal-skin region.

In some embodiments, each portable electronic device 100 can further synchronize the content of its database 145 to the server 610, where the server 610 also includes a patient database 615 to record the username, the wound location, and history files of the output wound images and their time information, size information, and severity, that are obtained from each portable electronic device 100. In addition, the server 610 may further sort the usernames of different patients according to the aforementioned information stored in the patient database 615 to create a care list for the medical staff to view on the server 610.

Figure 7A:
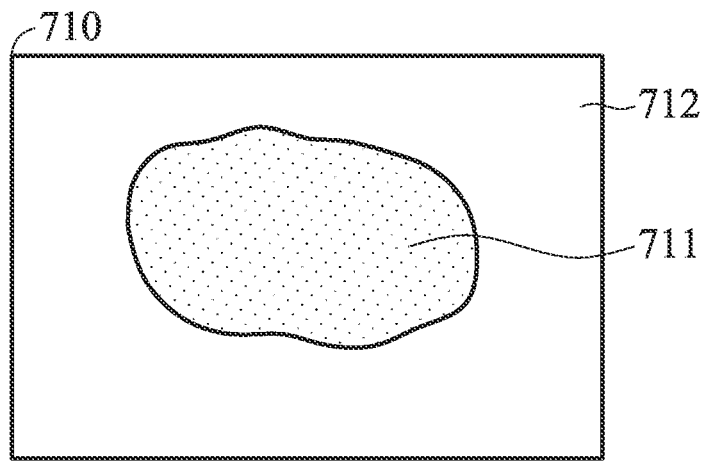
FIGS. 7A and 7B are diagrams of different severities and areas of the wound region in accordance with an embodiment of the disclosure.

For example, if a recently captured output wound image of a patient has a relatively large area and high severity (i.e., having a longer Euclidean distance and a lower similarity), the server 610 may prioritize this patient in the care list. As shown in FIG. 7A, assuming that the averages ($W\_R_{avg}$, $W\_G_{avg}$, $W\_B_{avg}$) of the red sub-pixels, green sub-pixels, and blue sub-pixels in the wound region 711 of the output wound image 710 are (230, 172, 148) and the averages ($N\_R_{avg}$, $N\_G_{avg}$, $N\_B_{avg}$) of the red sub-pixels, green sub-pixels, and blue sub-pixels in the normal-skin region 712 of the output wound image 710 are (160, 106, 92), the wound-measuring program 142 may calculate the severity of the wound region 711 using equation (9), where the severity (Euclidean distance)= $\sqrt{(160-230)^2+(106-172)^2+(92-148)^2}$=112. If the severity is greater than a preset threshold (e.g., 70, but not limited), the wound-measuring program 142 may determine that the wound region 711 is a more serious wound area.

Figure 7B:
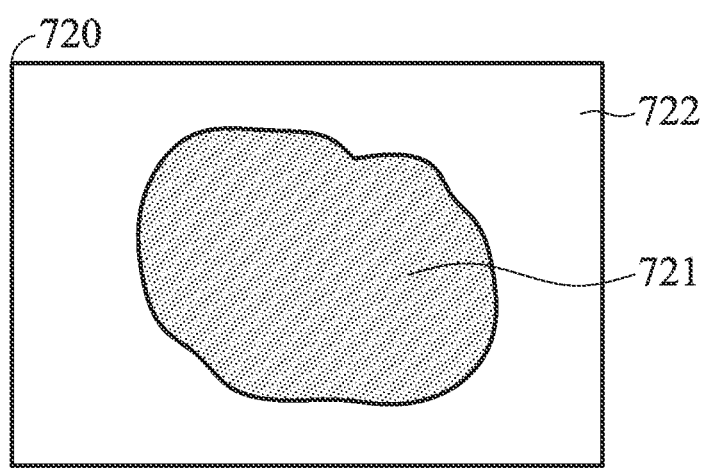

If a recently captured output wound image of a patient has a relatively small area and lower severity (i.e., having a shorter Euclidean distance and a higher similarity), the server 610 may place this patient in the lower position of the care list. As shown in FIG. 7B, assuming that the averages (W_$R_{avg}$, W_$G_{avg}$, W_$B_{avg}$) of the red sub-pixels, green sub-pixels, and blue sub-pixels in the wound region 711 of the output wound image 710 are (169, 114, 121) and the averages (N_$R_{avg}$, N_$G_{avg}$, N_$B_{avg}$) of the red sub-pixels, green sub-pixels, and blue sub-pixels in the normal-skin region 712 of the output wound image 710 are (176, 143, 119), the wound-measuring program 142 may calculate the severity of the wound region 711 using equation (9), where the severity (Euclidean distance)= $\sqrt{(176-169)^2+(143-114)^2+(119-121)^2}$=8. If the severity is lower than a preset threshold (e.g., 70, but not limited), the wound-measuring program 142 may determine that the wound region 711 is a less serious wound area.

For example, the wound-measuring program 142 can compare the size information and severity of the current output wound image with those of a previous output wound image obtained from previous one or more photographs. In an embodiment, when the area of the current output wound image of the portable electronic device 100 is larger than the area of the previous output wound image by a predetermined ratio (e.g., 5, not limited), the wound-measuring program 142 may determine that the wound of the user of the portable electronic device 100 is showing signs of enlargement, so the wound-measuring program 142 will notify the server 710 to add the username of the portable electronic device 100 (e.g., Zhang San) to the care list, and set a warning notice in the care list to show the "area" as an icon for the medical staff to check.

In addition, when the severity of the current output wound image of the portable electronic device 100 is greater than that of the previous output wound image by a predetermined ratio (e.g., 10%, not limited), the wound-measuring program 142 may determine that the wound of the user of the portable electronic device 100 is showing signs of deterioration, so the wound-measuring program 142 will notify the server 710 to add the username of the portable electronic device 100 (e.g., Zhang San) to the care list, and set a warning notice in the care list to show "serious" as an icon for the medical staff to check.

Figure 8:
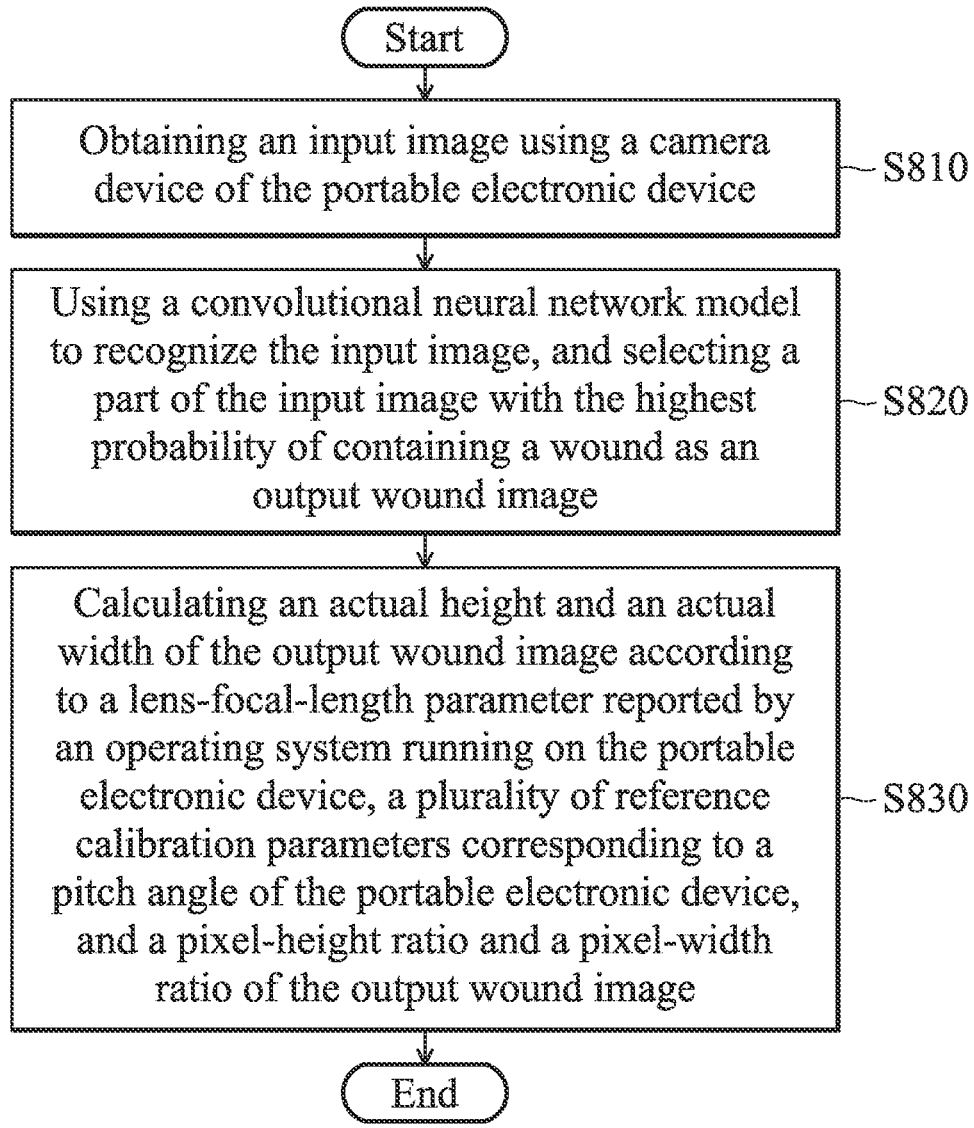
FIG. 8 is a flow chart of a wound-size measuring method in accordance with an embodiment of the disclosure.

FIG. 8 is a flow chart of a wound-size measuring method in accordance with an embodiment of the disclosure.

In step S810, the camera device 105 of the portable electronic device 100 is used to obtain an input image. For example, the camera device 105 focuses on and takes a picture of the user's wound at a first pitch angle to obtain an input image. For example, when the portable electronic device 100 is used to take a picture, the pitch angle of the portable electronic device 100 can be changed from 0 degrees to 90 degrees, and the inertial-measurement unit 170 can detect change of the pitch angle of the portable electronic device 100.

In step S820, the computation unit 120 uses the CNN model 143 to recognize the input image, and selects a part of the input image with the highest probability of containing a wound as the output wound image. The computation unit 120 may use the RPN model 144 to divide the input image into a plurality of first bounding boxes, and filter out a plurality of second bounding boxes with probabilities of containing wounds greater than a preset threshold. For example, as shown in FIG. 2D, during the image-recognition phase, the input image 210 is extracted by the CNN model 143 to obtain a feature map 1431, and the RPN model 144 can divide the input 210 into a plurality of first bounding boxes 211. In addition, the RPN model 144 can set a threshold probability. If the probability that the first bounding box 211 contains a wound is greater than the threshold probability, the RPN model 144 puts the first bounding box 211 into the proposals (i.e., candidate region), wherein the first bounding boxes 211 in the proposals are the second bounding boxes 212, as shown in FIG. 2E.

In step S830, the computation unit 120 calculates the actual height and actual width of the output wound image using the lens-focal-length parameter reported by the operating system 141 of the portable electronic device 100, a plurality of reference calibration parameters corresponding to the pitch angle of the portable electronic device 100, and the pixel-height ratio and pixel-width ratio (e.g., being displayed on the display panel 160) of the output wound image. For example, when the first pitch angle of the portable electronic device 100 is between 0 degrees and 45 degrees, the wound-measuring program 142 may use the reference calibration parameters obtained in the horizontal-calibration process to be used in equation (7) and equation (8) to calculate the target-object actual height $h_m$ and target-object actual width $w_m$ (e.g., expressed in centimeters). When the first pitch angle of the portable electronic device 100 is greater than or equal to 45 degrees or is between 45 to 90 degrees, the wound-measuring program 142 may use the reference calibration parameters obtained in the vertical-calibration process to be used in equation (7) and equation (8) to calculate the target-object actual height $h_m$ and target-object actual width $w_m$ (e.g., expressed in centimeters).

In view of the above, a portable electronic device and a wound-size measuring method are provided, which are capable of calculating the actual height and actual width of the output wound image using the lens-focal-length parameter reported by the operating system of the portable electronic device, a plurality of calibration parameters corresponding to the first pitch angle, and the pixel-height ratio and pixel-width ratio of the output wound image. The reference calibration parameters can be obtained from the horizontal-calibration process and the vertical-calibration process of the portable electronic device.

The portable electronic device and wound-size measuring method in the disclosure can accurately calculate the actual height, actual width, and area of the wound region in the input image in an objective manner, and can calculate the severity of the wound region. In addition, the portable electronic device and the wound-size measuring method in the disclosure can compare the area or severity of the current output wound image with that of the previous output wound image taken previously, so as to determine whether there are signs of expansion or deterioration of the wound region, and then a warning notice can be sent to the server for medical staff to conduct related inspections, so that such patient can be taken care of.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having the same name (but for use of the ordinal term) to distinguish the claim elements.

While the disclosure has been described by way of example and in terms of the preferred embodiments, it should be understood that the disclosure is not limited to the disclosed embodiments. On the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A portable electronic device, comprising:
   an inertial-measurement unit, configured to detect a pitch angle of the portable electronic device;
   a camera device, configured to obtain an input image;
   a storage device, configured to store an operating system, a wound-measuring program, a CNN (convolutional neural network) model, and an RPN (regional proposal network) model; and
   a processor, configured to execute the wound-size measuring program to perform the following steps:
   using the CNN model to recognize the input image, and to select a part of the input image with the highest probability of containing a wound as an output wound image; and
   calculating an actual height and an actual width of the output wound image according to a lens-focal-length parameter reported by the operating system, a plurality of reference calibration parameters corresponding to the pitch angle, and a pixel-height ratio and a pixel-width ratio of the output wound image;
   wherein the processor further performs a machine-learning clustering algorithm to divide the output wound image into a wound region and a normal-skin region,
   wherein the processor further calculates a first pixel number in the output wound image and a second pixel number in the wound region, and divides the second pixel number by the first pixel number to obtain a wound-region pixel ratio,
   wherein the processor further multiplies the actual height of the output wound image by the actual width of the output wound image to obtain an actual area of the output wound image, and multiplies the actual area by the wound-region pixel ratio to obtain an actual area of the wound region.

2. The portable electronic device as claimed in claim 1, wherein the reference calibration parameters comprise a reference-object actual height, a reference-object actual width, a reference-object pixel-height ratio, and a reference-object focal distance.

3. The portable electronic device as claimed in claim 2, wherein during a horizontal-calibration process of the wound-measuring program, the portable electronic device takes a picture of a reference object at the pitch angle of 0 degrees to obtain a first reference-object image, and obtains a first reference-object focal distance from an API (application programming interface) of the operating system, and the reference object has the reference-object actual height and the reference-object actual width,
   wherein during a vertical-calibration process of the wound-measuring program, the portable electronic device takes another picture of the reference object at the pitch angle of 90 degrees to obtain a second reference-object image, and the processor obtains a second reference-object focal distance from the API of the operating system,
   wherein the processor divides a first pixel height of the first reference-object image or the second reference-object image displayed on a display panel of the portable electronic device by a second pixel height of the display panel to obtain a first reference-object pixel-height ratio or a second reference-object pixel-height ratio.

4. The portable electronic device as claimed in claim 3, wherein in response to the pitch angle being between 0 and 45 degrees, the processor uses the first reference-object focal distance as the reference-object focal distance, and uses the first reference-object pixel-height ratio as the reference-object pixel-height ratio;
   wherein in response to the pitch angle being between 45 and 90 degrees, the processor uses the second reference-object focal distance as the reference-object focal distance, and uses the second reference-object pixel-height ratio as the reference-object pixel-height ratio.

5. The portable electronic device as claimed in claim 4, wherein the processor calculates equation (1) and equation (2) to obtain the actual height and the actual width of the output wound image, where equation (1) and equation (2) are expressed as follows:

$$h_m = h_c \times \frac{g_c \times p_m}{g_m \times p_c} \qquad (1)$$

$$w_m = w_c \times \frac{g_c \times p_m}{g_m \times p_c} \qquad (2)$$

where hc denotes the reference-object actual height; gc denotes the reference-object focal distance; pc denotes the reference-object pixel-height ratio; hm denotes the actual height of the output wound image; gm denotes the lens-focal-length parameter; pm denotes the pixel-height ratio; wm denotes the actual width of the output wound image; and wc denotes the reference-object actual width.

6. The portable electronic device as claimed in claim 1, wherein the processor further calculates a first red average, a first green average, and a first blue average of a red sub-pixel, a green sub-pixel, and a blue sub-pixel of each pixel in the wound region, and calculates a second red average, a second green average, and a second blue average of a red sub-pixel, a green sub-pixel, and a blue sub-pixel of each pixel in the normal-skin region,
   wherein the processor calculates a Euclidean distance between the wound region and the normal-skin region to represent the severity of the wound region according to the first red average, the first green average, the first blue average, the second red average, the second green average, and the second blue average.

7. The portable electronic device as claimed in claim 6, wherein in response to the processor determining that the actual area of the output wound image is larger than the actual area of a previous output wound image by a first predetermined ratio, the processor informs a server to add a username of the portable electronic device into a care list for medical staff to conduct related inspections.

8. The portable electronic device as claimed in claim 6, wherein in response to the processor determining that the severity of the output wound image is greater than the severity of a previous output wound image by a second predetermined ratio, the processor informs a server to add a username of the portable electronic device into a care list for medical staff to conduct related inspections.

9. The portable electronic device as claimed in claim 1, wherein before the processor uses the CNN model to recognize the input image, the processor uses the RPN model to generate a plurality of first bounding boxes using the input image, and filters out a plurality of second bounding boxes with probabilities of being a wound greater than a predetermined value from the first bounding boxes,
wherein the CNN model selects the second bounding box with the highest probability of being a wound as the output wound image.

10. A wound-size measuring method, for use in a portable electronic device, wherein the portable electronic device comprises a display panel and a camera device, the method comprising:
obtaining an input image via the camera device;
using a CNN (convolutional neural network) model to recognize the input image, and selecting a part of the input image with the highest probability of containing a wound as an output wound image;
calculating an actual height and an actual width of the output wound image according to a lens-focal-length parameter reported by an operating system running on the portable electronic device, a plurality of reference calibration parameters corresponding to a pitch angle of the portable electronic device, and a pixel-height ratio and a pixel-width ratio of the output wound image;
performing a machine-learning clustering algorithm to divide the output wound image into a wound region and a normal-skin region;
calculating a first pixel number in the output wound image and a second pixel number in the wound region, and dividing the second pixel number by the first pixel number to obtain a wound-region pixel ratio; and
multiplying the actual height of the output wound image by the actual width of the output wound image to obtain an actual area of the output wound image, and multiplying the actual area by the wound-region pixel ratio to obtain an actual area of the wound region.

11. The method as claimed in claim 10, wherein the reference calibration parameters comprise a reference-object actual height, a reference-object actual width, a reference-object pixel-height ratio, and a reference-object focal distance.

12. The method as claimed in claim 11, wherein during a horizontal-calibration process of the wound-measuring program, the portable electronic device takes a picture of a reference object at the pitch angle of 0 degrees to obtain a first reference-object image, and obtains a first reference-object focal distance from an API (application programming interface) of the operating system, and the reference object has the reference-object actual height and the reference-object actual width,
wherein during a vertical-calibration process of the wound-measuring program, the portable electronic device takes another picture of the reference object at the pitch angle of 90 degrees to obtain a second reference-object image, and obtains a second reference-object focal distance from the API of the operating system,
wherein the method further comprises: dividing a first pixel height of the first reference-object image or the second reference-object image displayed on the display panel by a second pixel height of the display panel to obtain a first reference-object pixel-height ratio or a second reference-object pixel-height ratio.

13. The method as claimed in claim 12, further comprising:
in response to the pitch angle being between 0 and 45 degrees, using the first reference-object focal distance as the reference-object focal distance, and using the first reference-object pixel-height ratio as the reference-object pixel-height ratio; and
in response to the pitch angle being between 45 and 90 degrees, using the second reference-object focal distance as the reference-object focal distance, and using the second reference-object pixel-height ratio as the reference-object pixel-height ratio.

14. The method as claimed in claim 13, further comprising:
calculating equation (1) and equation (2) to obtain the actual height and the actual width of the output wound image, where equation (1) and equation (2) are expressed as follows:

$$h_m = h_c \times \frac{g_c \times p_m}{g_m \times p_c} \qquad (1)$$

$$w_m = w_c \times \frac{g_c \times p_m}{g_m \times p_c} \qquad (2)$$

where hc denotes the reference-object actual height; gc denotes the reference-object focal distance; pc denotes the reference-object pixel-height ratio; hm denotes the actual height of the output wound image; gm denotes the lens-focal-length parameter; pm denotes the pixel-height ratio; wm denotes the actual width of the output wound image; and wc denotes the reference-object actual width.

15. The method as claimed in claim 10, further comprising:
calculating a first red average, a first green average, and a first blue average of a red sub-pixel, a green sub-pixel, and a blue sub-pixel of each pixel in the wound region;
calculating a second red average, a second green average, and a second blue average of a red sub-pixel, a green sub-pixel, and a blue sub-pixel of each pixel in the normal-skin region; and
calculating a Euclidean distance between the wound region and the normal-skin region to represent the severity of the wound region according to the first red average, the first green average, the first blue average, the second red average, the second green average, and the second blue average.

16. The method as claimed in claim 15, further comprising:
in response to a determination that the actual area of the output wound image is larger than the actual area of a previous output wound image by a first predetermined ratio, informing a server to add a username of the portable electronic device into a care list for medical staff to conduct related inspections.

17. The method as claimed in claim 15, further comprising:
in response to a determination that the severity of the output wound image is greater than the severity of a previous output wound image by a second predetermined ratio, informing a server to add a username of the portable electronic device into a care list for medical staff to conduct related inspections.

18. The method as claimed in claim 10, wherein before using the CNN model to recognize the input image, the method further comprises:
    using the RPN model to generate a plurality of first bounding boxes using the input image, and filtering out a plurality of second bounding boxes with probabilities of being a wound greater than a predetermined value from the first bounding boxes; and
    using the CNN model to select the second bounding box with the highest probability of being a wound as the output wound image.

19. The portable electronic device as claimed in claim 1, wherein the processor further performs the machine-learning clustering algorithm to group each pixel of the output wound image, so as to divide the output wound image into the wound region and the normal-skin region.

20. The method as claimed in claim 10, wherein the step of performing the machine-learning clustering algorithm to divide the output wound image into the wound region and the normal-skin region comprises:
    performing the machine-learning clustering algorithm to group each pixel of the output wound image, so as to divide the output wound image into the wound region and the normal-skin region.

* * * * *